United States Patent
Zerban et al.

(10) Patent No.: US 7,459,566 B2
(45) Date of Patent: Dec. 2, 2008

(54) 1,2,4-OXADIAZOL-5-ONE-4-(BENZIMIDAZO LYLMETHYLAMINO)BENZAMIDINE COMPOUNDS

(75) Inventors: Georg Zerban, Ingelheim (DE); Arndt Hausherr, Mainz (DE); Kerstin Schlarb, Ingelheim (DE); Heinz-Peter Schmitt, Ingelheim (DE); Bjoern Weyell, Aspisheim (DE); Gunter Koch, Schwabenheim (DE); Rainer Hamm, Ingelheim (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 0 days.

(21) Appl. No.: 11/681,549

(22) Filed: Mar. 2, 2007

(65) Prior Publication Data

US 2007/0149589 A1 Jun. 28, 2007

Related U.S. Application Data

(62) Division of application No. 11/149,021, filed on Jun. 9, 2005, now Pat. No. 7,202,368.

(30) Foreign Application Priority Data

Jun. 25, 2004 (EP) .................. 04014917

(51) Int. Cl.
*C07D 271/06* (2006.01)
*C07D 235/06* (2006.01)
(52) U.S. Cl. ............... 548/273.4; 548/304.7; 546/273.4

(58) Field of Classification Search ............. 548/132, 548/304.7; 546/273.4
See application file for complete search history.

(56) References Cited

U.S. PATENT DOCUMENTS

| 6,248,770 | B1 | 6/2001 | Ries et al. | |
| 6,414,008 | B1 * | 7/2002 | Hauel et al. | ............ 514/394 |
| 6,451,832 | B2 | 9/2002 | Ries et al. | |
| 6,455,529 | B1 | 9/2002 | Gante et al. | |
| 6,593,355 | B2 | 7/2003 | Ries et al. | |

FOREIGN PATENT DOCUMENTS

| AU | 763094 | 1/2000 |
| DE | 199 62 329 | 6/2001 |
| WO | WO 00/01704 | 1/2000 |

OTHER PUBLICATIONS

Abstract of WO 2005-EP2881, Boeckel et al. and STN search report.*
N-tosylation of amine and alcohol, on-line PDF file from www.chm.davidson.edu/erstevens/202lab1.pdf.*
Abstract for DE 199 62 329 A1.

* cited by examiner

*Primary Examiner*—Rei-tsang Shiao
*Assistant Examiner*—Yong Chu
(74) *Attorney, Agent, or Firm*—Michael P. Morris; Mary-Elllen M. Devlin; Wendy A. Petka

(57) ABSTRACT

A process for preparing an optionally substituted 4-benzimidazol-2-ylmethylamino)benzamidine, the process comprising:
(a) condensing an optionally suitably substituted diaminobenzene with 2-[4-(1,2,4-oxadiazol-5-on-3-yl)phenylamino]acetic acid;
(b) hydrogenating the product obtained from step (a); and
(c) optionally carboxylating the amidino group of the product obtained from step (b).

4 Claims, No Drawings

1,2,4-OXADIAZOL-5-ONE-4-(BENZIMIDAZOLYLMETHYLAMINO)BENZAMIDINE COMPOUNDS

RELATED APPLICATIONS

This application is a divisional application of U.S. application Ser. No. 11/149,021, filed Jun. 9, 2005, now U.S. Pat. No. 7,202,368, which claims priority to European Application No. EP 04 014 917.1, filed Jun. 25, 2004, the contents of which are hereby incorporated by reference in their entirety.

FIELD OF THE INVENTION

The invention relates to a process for preparing an optionally substituted 4-(benzimidazol-2-ylmethylamino)benzamidine, wherein:

(a) an optionally suitably substituted diaminobenzene is condensed with 2-[4-(1,2,4-oxadiazol-5-one-3-yl)phenylamino]acetic acid;

(b) the product thus obtained is hydrogenated; and (c) optionally the amidino group is carbonylated.

BACKGROUND OF THE INVENTION

Substituted (4-benzimidazol-2-ylmethylamino)benzamidines, particularly 1-methyl-2-[N-[4-(N-n-hexyloxycarbonylamidino)phenyl]aminomethyl]benzimidazol-5-yl-carboxylic acid-N-(2-pyridyl)-N-(2-ethoxycarbonylethyl) amides are already known from International Patent Application WO 98/37075 as active substances with a thrombin-inhibiting and thrombin time-prolonging activity.

The main field of indications for the compound of chemical formula I is the postoperative prevention of deep vein thrombosis.

In WO 98/37075 it is proposed to prepare substituted (4-benzimidazol-2-ylmethylamino)benzamidines by reacting the corresponding, substituted (4-benzimidazol-2-ylmethylamino)benzonitriles with ammonia. This method is very onerous in terms of production costs and results in a high load of acids requiring disposal.

The aim of the present invention was to indicate an alternative method of preparing the substituted (4-benzimidazol-2-ylmethylamino)benzamidines, by which this onerous stage of the production process could be avoided.

SUMMARY OF THE INVENTION

Surprisingly, it has now been found that the substituted 4-(benzimidazol-2-ylmethylamino)benzamidines can be prepared in high yields and using inexpensive adjuvants if:

(a) an optionally suitably substituted diaminobenzene is condensed with 2-[4-(1,2,4-oxadiazol-5-one-3-yl)phenylamino]acetic acid;

(b) the product thus obtained is hydrogenated; and (c) optionally the amidino group is carbonylated, preferably with an alkylhalogen formate, in the presence of a base, particularly with hexyl chloroformate.

The invention also relates to the new intermediate products of formula III involved in the process according to the invention:

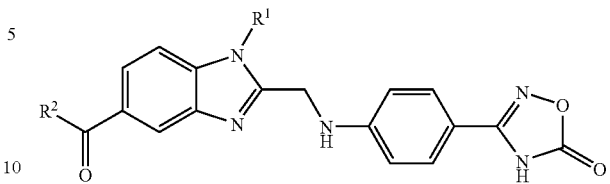

(III)

wherein $R^1$ and $R^2$ have the meanings given for the subsequent compounds of formula (I), and also 2-[-4-(1,2,4-oxadiazol-5-one-3-yl)phenylamino]acetic acid, and 4-(1,2,4-oxadiazol-5-one-3-yl)aniline.

DETAILED DESCRIPTION OF THE INVENTION

Preferably the invention relates to a process for preparing an optionally substituted 4-(benzimidazol-2-ylmethylamino) benzamidine of formula (I)

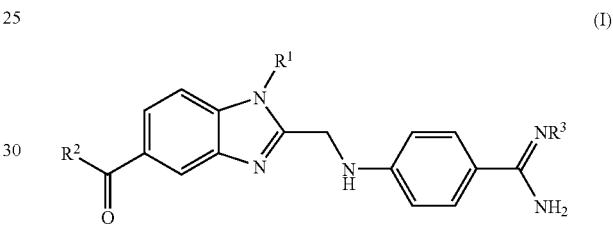

(I)

wherein:
$R^1$ denotes a $C_{1-6}$-alkyl or $C_{3-7}$-cycloalkyl group;
$R^2$ denotes:
  (i) a $C_{1-6}$-alkyl group or a $C_{3-7}$-cycloalkyl group optionally substituted by a $C_{1-3}$-alkyl group, while the $C_{1-3}$-alkyl group may additionally be substituted by a carboxyl group or by a group which may be converted in vivo into a carboxy group, or
  (ii) an $R^{21}NR^{22}$ group, wherein:
    $R^{21}$ denotes a $C_{1-6}$ alkyl group which may be substituted by a carboxy, $C_{1-6}$ alkoxycarbonyl, benzyloxycarbonyl, $C_{1-3}$-alkylsulfonylaminocarbonyl, phenylsulfonylaminocarbonyl, trifluorosulfonylamino, trifluorosulfonylaminocarbonyl, or 1H-tetrazolyl group, a $C_{2-4}$-alkyl group substituted by a hydroxy, phenyl-$C_{1-3}$-alkoxy, carboxy-$C_{1-3}$-alkylamino, $C_{1-3}$-alkoxycarbonyl-$C_{1-3}$-alkylamino, N-($C_{1-3}$-alkyl)-carboxy-$C_{1-3}$-alkylamino or N-($C_{1-3}$-alkyl)-$C_{1-3}$-alkoxycarbonyl-$C_{1-3}$-alkylamino group, while in the above-mentioned groups the α-carbon atom to the adjacent nitrogen atom may not be substituted, or a piperidinyl group optionally substituted by a $C_{1-3}$-alkyl group, and
    $R^{22}$ denotes a hydrogen atom, a $C_{1-6}$-alkyl group, a $C_{3-7}$-cycloalkyl group optionally substituted by a $C_{1-3}$-alkyl group, a $C_{3-6}$-alkenyl or $C_{3-6}$-alkynyl group, while the unsaturated moiety may not be linked directly to the nitrogen atom of the $R^{21}NR^{22}$ group, a phenyl group optionally substituted by a fluorine, chlorine or bromine atom or by a $C_{1-3}$-alkyl or $C_{1-3}$-alkoxy group, a benzyl, oxazolyl, isoxazolyl, thiazolyl, isothiazolyl, pyrazolyl, pyridinyl, pyrimidinyl, pyrazinyl, pyridazinyl, pyrrolyl, thienyl or imidazolyl group optionally substituted by a $C_{1-3}$-alkyl group, or $R^{21}$ and $R^{22}$ together with the nitrogen atom between them denote a 5- to 7-membered cycloakyleneimino group optionally substituted by a carboxy or $C_{1-4}$-alkoxycarbonyl group, to which a phenyl ring may additionally be fused; and $R^3$ denotes a hydrogen atom, a $C_{1-9}$-alkoxycarbonyl, cyclohexyloxycarbonyl, phenyl-$C_{1-3}$-alkoxycarbonyl, benzoyl, p-$C_{1-3}$-alkyl-benzoyl or pyridinoyl group, while the ethoxy moiety in the 2 position of the above-mentioned $C_{1-9}$-alkoxycarbonyl group may additionally be substituted by a $C_{1-3}$-alkylsulfonyl or 2-($C_{1-3}$-alkoxy)-ethyl group, while in step (a) a phenyldiamine of formula (II)

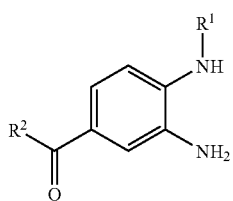

(II)

wherein $R^1$ and $R^2$ have the meanings given for formula (I), is reacted with 2-[4-(1,2,4-oxadiazol-5-one-3-yl)phenylamino]acetic acid, the resulting product of formula (III)

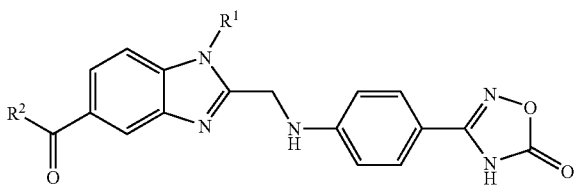

(III)

wherein $R^1$ and $R^2$ have the meanings given for formula (I), is hydrogenated in step (b), and (c) optionally the compound of formula (I) thus obtained wherein $R^3$ denotes hydrogen, is reacted with a compound of formula (IV)

(IV)

wherein $R^3$ has the meaning given for formula (I), and X denotes a suitable leaving group.

The process according to the invention is particularly preferably used to prepare the compounds of formula (I) wherein:

$R^1$ denotes a $C_{1-3}$-alkyl group;

$R^2$ denotes a $R^{21}NR^{22}$ group, wherein:
  $R^{21}$ denotes a $C_{1-3}$ alkyl group which may be substituted by a carboxy or $C_{1-3}$ alkoxycarbonyl, and
  $R^{22}$ denotes a hydrogen atom, a $C_{1-3}$ alkyl group, or a pyridinyl group optionally substituted by a $C_{1-3}$-alkyl group; and $R^3$ denotes a hydrogen atom or a $C_{1-8}$-alkoxycarbonyl group.

Most preferably the process according to the invention is used to prepare the compound of formula (I) wherein:

$R^1$ denotes a methyl group;

$R^2$ denotes an $R^{21}NR^{22}$ group, wherein:

$R^{21}$ denotes an ethyl group which is substituted by an ethoxycarbonyl group, and $R^{22}$ denotes a pyridin-2-yl group; and $R^{23}$ denotes a hexyloxycarbonyl group.

The following embodiments (A) to (E) of the process according to the invention are preferred:

(A) The condensation step (a) is carried out in the presence of an inert diluent and a water-binding agent. The correspondingly substituted diaminobenzenes of formula (II) are known, for example, from International Patent Application WO 98/37075 or may be prepared analogously to those described therein. It is particularly preferable to use 3-amino-4-methylaminobenzoic acid amides, especially 3-amino-4-methylaminobenzoic acid-N-(2-pyridyl)-N-(2-ethoxycarbonylethyl)amides.

The inert diluents used may be both aprotic apolar solvents such as, e.g., aliphatic or aromatic, optionally halogenated hydrocarbons, or aprotic polar solvents such as, e.g., ethers and/or amides or lactams and/or mixtures thereof. Aprotic apolar solvents used are preferably branched or unbranched $C_5$-$C_8$ aliphatic alkanes, $C_4$-$C_{10}$ cycloalkanes, $C_1$-$C_6$ aliphatic haloalkanes, $C_6$-$C_{10}$ aromatic alkanes or mixtures thereof. It is particularly preferable to use alkanes such as pentane, hexane, or heptane, cycloalkanes such as cyclohexane or methylcyclohexane, haloalkanes such as dichloromethane, aromatic alkanes such as benzene, toluene, or xylene, or mixtures thereof. Suitable aprotic solvents are polar ethers such as, for example, tetrahydrofuran (THF), methyltetrahydrofuran, dioxane, tert-butylmethylether, or dimethoxyethylether, or amides such as, for example, dimethylformamide, or lactams such as, for example, N-methylpyrrolidone.

The water-binding agents used may be hygroscopic salts, inorganic or organic acids or the acid chlorides thereof, anhydrides of inorganic or organic acids, anhdyrides of alkanephosphonic acids, molecular sieves or urea derivatives. 1,1'-Carbonyldiimidazoles and alkanephosphonic anhydrides are preferred, while alkanephosphonic anhydrides are particularly preferred.

In a preferred embodiment 1,1'-carbonyldiimidazole is suspended in THF and heated. 2-[4-(1,2,4-oxadiazol-5-one-3-yl)phenylamino]acetic acid is added. The correspondingly substituted diaminobenzene is added in THF. The reaction mixture is stirred at about 50° C. and then after the addition of acetic acid, it is evaporated down, combined with water, and the solid substance is filtered off, washed, and dried.

In a second particularly preferred embodiment alkanephosphonic anhydrides are added in the presence of an organic base, preferably a tertiary amine, such as, e.g., DIPEA, to a solution of 2-[4-(1,2,4-oxadiazol-5-one-3-yl)phenylamino]acetic acid and correspondingly substituted diaminobenzene in THF. The reaction mixture is stirred, preferably at temperatures between –10° C. and 50° C., and then, after the addition of acetic acid, it is evaporated down. It is combined with ethanol and filtered while hot. Then the substance precipitated from the cooled solution is filtered off, washed, and dried.

(B) The hydrogenation in step (b) is carried out in the presence of an inert diluent and a hydrogenation catalyst. In a particularly preferred process, the hydrogenation is carried out in a temperature range from 0° C. to 100° C., preferably from 0° C. to 50° C., particularly from 10° C. to 30° C.

Also preferred is a process wherein the hydrogenation is carried out under a pressure of more than 0.5 bar to 100 bar, preferably under a pressure of 1 bar to 10 bar, particularly at about 1 to 2 bar.

The inert diluents used may be both protic solvents such as, e.g., alcohols, carboxylic acids, and/or water, or aprotic polar solvents such as, e.g., ether and/or amides or lactams and/or mixtures thereof. Water may optionally be added to all the solvents. Preferred protic solvents used are branched or unbranched $C_1$-$C_8$ alkanols, $C_1$-$C_3$ carboxylic acids, or mixtures thereof. Particularly preferably, lower alcohols such as methanol, ethanol, n-propanol, and isopropanol, carboxylic acids such as formic acid, acetic acid, and propionic acid, or mixtures thereof are used. The particularly preferred reaction medium is ethanol and/or acetic acid, which may optionally contain water. Suitable aprotic solvents are polar ethers such as, for example, tetrahydrofuran or dimethoxyethylether or amides such as, for example, dimethylformaide, or lactams such as, for example, N-methylpyrrolidone. It is preferable to use solvents which have low tendencies to flammability.

Suitable hydrogenation catalysts are generally transition metals such as, for example, nickel, platinum, or palladium, or the salts or oxides thereof. Raney nickel, platinum oxide, and palladium on an inert carrier material, particularly palladium on activated charcoal (Pd/C), are preferred.

Preferred processes are those wherein during the hydrogenation the product of step (a) is used in a ratio by weight of from 1:1 to 1000:1, preferably from 5:1 to 100:1 to the hydrogenation catalyst.

In a preferred embodiment the product of step (a) is taken up in ethanol and, after the addition of acetic acid, hydrogenated with water-dampened 10% Pd/C at ambient temperature and at 2 bar hydrogen. The catalyst is filtered off and p-toluenesulfonic acid dissolved in 90 mL of ethanol or in 90 mL of water is added to the filtrate. Preferably an aqueous p-toluenesulfonic acid solution is used. The tosylate of the 4-(benzimidazol-2-ylmethylamino)benzamidine obtained is precipitated out, filtered off, and washed with ethanol in several batches.

In a particularly preferred embodiment the product of step (a) is taken up in ethanol/water and hydrogenated with water-dampened 10% Pd/C at ambient temperature and at 2 bar hydrogen. The catalyst is filtered off and p-toluenesulfonic acid (solid or dissolved in 90 mL of ethanol or in 90 mL of water) is added to the filtrate. Preferably solid p-toluenesulfonic acid is used. The tosylate of the 4-(benzimidazol-2-ylmethylamino)benzamidine obtained is precipitated out, filtered off, and washed with ethanol in several batches.

(C) In order to prepare 2-[4-(1,2,4-oxadiazol-5-one-3-yl)phenylamino]acetic acid, 4-(1,2,4-oxadiazol-5-one-3-yl)aniline is reacted with a 2-haloacetic acid ester, preferably ethyl bromoacetate, in the presence of a weak base, preferably a tertiary amine, such as, for example, triethylamine or an alkali metal carbonate, such as, for example, sodium carbonate in an inert solvent, and the 2-4-(1,2,4-oxadiazol-5-one-3-yl)phenylamino]acetic acid ester obtained is saponified.

The inert diluents used may be either protic solvents such as, e.g., alcohols and/or water, or aprotic polar solvents such as, e.g., ether and/or amides or lactams and/or mixtures thereof. Water may optionally be added to all the solvents. Preferred protic solvents used are water or branched or unbranched $C_1$-$C_8$ alkanols or mixtures thereof. Particularly preferably, water or lower alcohols such as methanol, ethanol, n-propanol, and isopropanol, or mixtures thereof are used. The particularly preferred reaction medium is ethanol, which may optionally contain water. Isopropanol, optionally together with water, may also be used. However, the most suitable solvent is water. Suitable aprotic solvents are polar ethers such as, for example, tetrahydrofuran or dimethoxyethylether or amides such as, for example, dimethylformamide, or lactams such as, for example, N-methylpyrrolidone.

In a particularly preferred embodiment ethyl bromoacetate is metered into a suspension of 4-(1,2,4-oxadiazol-5-one-3-yl)aniline and sodium carbonate in water/isopropanol or preferably in water/ethanol and stirred. The cooled suspension is suction filtered, washed with water and ethanol in several batches, and dried.

The saponification is preferably carried out in a protic solvent with an alkali metal or alkaline earth metal hydroxide, particularly with lithium, sodium, or potassium hydroxide.

In a particularly preferred embodiment 2-[4-(1,2,4-oxadiazol-5-one-3-yl)phenylamino]acetic acid ester is suspended in water or preferably in water/ethanol and an aqueous solution of NaOH is slowly added at ambient temperature. The suspension changes into a solution and is heated to 45° C. to 75° C. HCl is added to the solution thus obtained until a pH of about 5 or preferably 3 is achieved. The solid is isolated and washed with cold water and cold ethanol and MtBE.

(D) In order to prepare 4-(1,2,4-oxadiazol-5-one-3-yl)aniline, aminophenylamidoxime is reacted with a dialkylcarbonate, preferably dimethylcarbonate or diethyl carbonate, in the presence of a base, preferably an alkali metal alkoxide, particularly sodium methoxide, sodium ethoxide, or potassium tert-butoxide.

4-Aminophenylamidoxime may be prepared, for example, by reacting 4-aminobenzonitrile with hydroxylamine hydrochloride.

In a particularly preferred embodiment, sodium methoxide is preferably sodium ethoxide is added at 65° C.-75° C., preferably at 70° C.-75° C., to a suspension of 4-aminophenylamidoxime in ethanol and rinsed with ethanol. After 15 minutes stirring, diethylcarbonate or preferably dimethylcarbonate is added dropwise. After 2-4 hours reaction, the mixture is cooled and ethanol is distilled off at 120 mbar and 40° C. The residue is taken up in water and, after heating, adjusted to pH 10-12 with semi-concentrated sodium hydroxide solution, then adjusted to pH<6, preferably to pH<4, more preferably to pH 2-3, by acidification with concentrated hydrochloric acid and slowly cooled. The solution change into a suspension, which is filtered and washed several times with cold water and ethanol.

The preparation of the 2-[4-(1,2,4-oxadiazol-5-one-3-yl)phenylamino]acetic acid required as an intermediate product from 4-aminobenzonitrile is illustrated in the reaction plan shown below.

Diagram I
The non-isolated intermediate stages indicated by square brackets may optionally vary between the different alternative embobiments of the process.
The diagram shows a preferred embodiment.
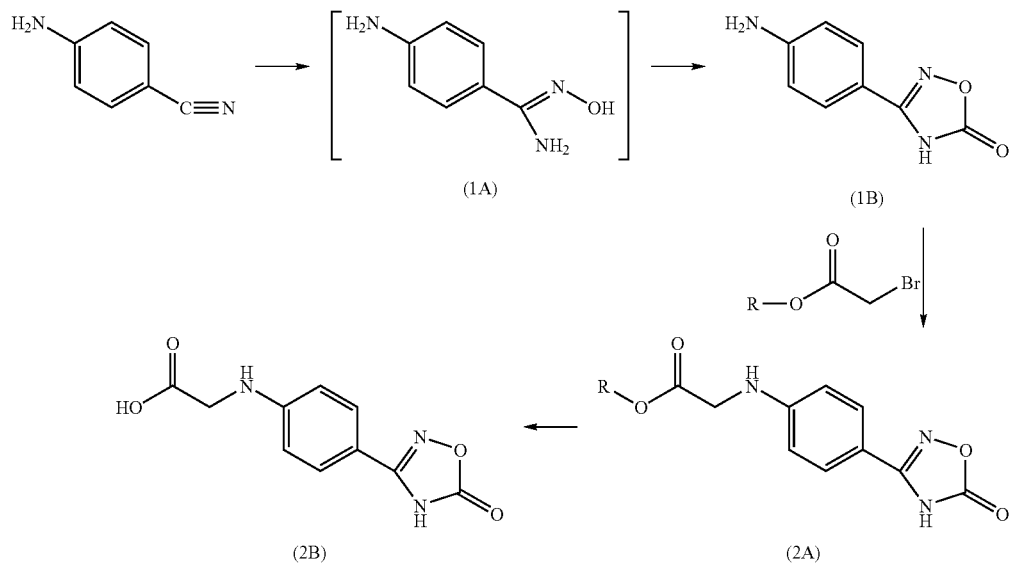
The preparation of a 4-(benzimidazol-2-ylmethylamino) benzamidine is illustrated by way of example in the following reaction plan.
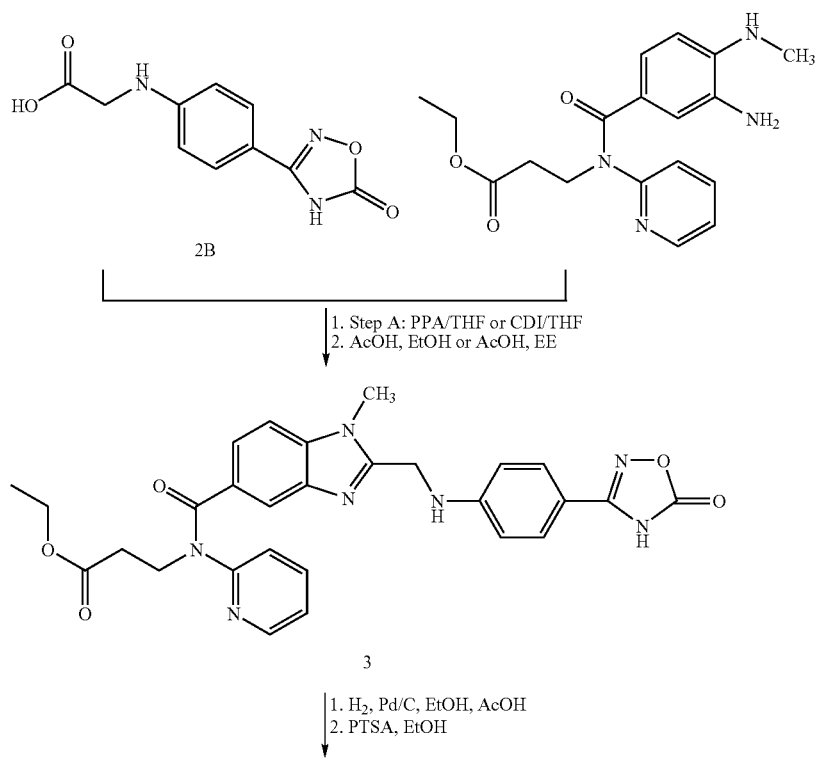

-continued

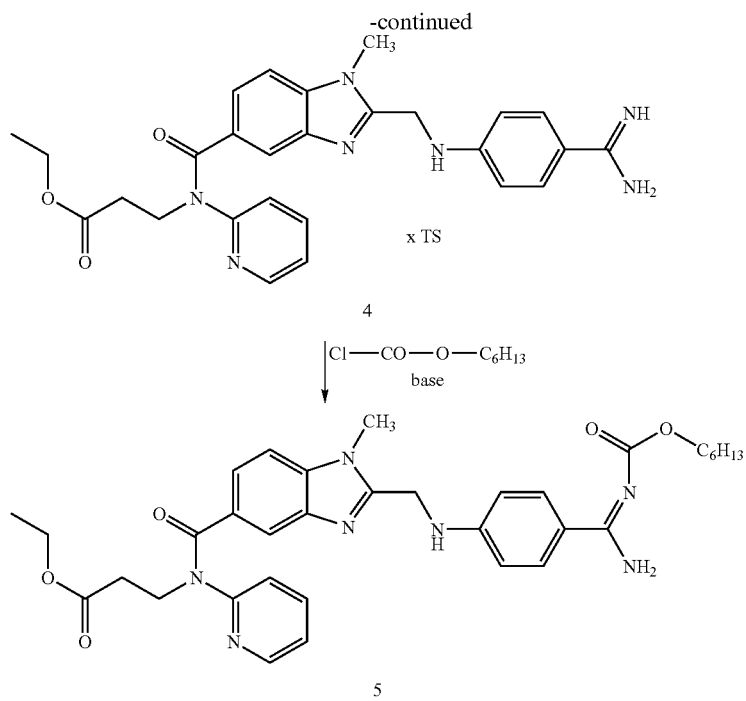

The working up of the individual reactions may be carried out in the conventional manner, e.g., by separating off the reaction adjuvants, eliminating the solvent, and isolating the pure end product from the residue by crystallization, distillation, extraction, or chromatography.

After the process described above, the compound of formula (I) thus obtained may be converted into a physiologically acceptable salt. The physiologically acceptable salts may be salts with inorganic or organic acids or, if the compound contains a carboxy group, salts with inorganic or organic bases. Possible acids for this purpose include, for example, methanesulfonic acid, hydrochloric acid, hydrobromic acid, sulfuric acid, phosphoric acid, fumaic acid, succinic acid, lactic acid, citric acid, tartaric acid, or maleic acid. Suitable bases include, for example, sodium hydroxide, potassium hydroxide, cyclohexylamine, ethanolamine, diethanolamine, and triethanolamine. The compound of formula (5) is preferably converted into the mesylate thereof.

The process according to the invention will now be illustrated by means of the Examples that follow. The skilled person will be aware that the Examples serve purely as an illustration and are not to be viewed in a limiting capacity.

EXAMPLES

The following abbreviations are used hereinbefore and hereinafter:
AcOH acetic acid
AMBPA 3-amino-4-methylaminobenozic acid-N-(2-pyridyl)-N-(2-ethoxycarbonylethyl)amide
CDI 1,1'-carbonyldiimidazole
DIPEA diisopropylethylamine
EE ethyl acetate
EtOH ethanol
HCl hydrochloric acid
MtBE methyl-tert-butyl ether
NaOH sodium hydroxide
NMP N-methylpyrrolidone
PPA propanephosphonic anhydride
PTSA p-toluenesulfonic acid
RT ambient (room) temperature
THF tetrahydrofuran
decomp. decomposition Example 1

Preparation of 4-(1,2,4-oxadiazol-5-one-3-yl)aniline (1)

Variant 1:
(1A)
In the reaction vessel, 118.6 g (1 mol) of 4-aminobenzonitrile and 68.9 g (0.65 mol) of sodium carbonate are placed in 500 mL of ethanol and 100 mL of water and heated to 60° C. 76.4 g (1.1 mol) of hydroxylamine hydrochloride dissolved in 100 mL of water is slowly added dropwise to this suspension. The mixture is then stirred overnight at 60° C. On cooling to 0° C.-5° C., the substance is precipitated out, filtered off, and washed several times with a total of 150 mL cold water and 100 mL cold ethanol. Finally, it is washed with 50 mL of MtBE and 178.4 g of damp product is obtained. This is dried in vacuo at 35° C. Yield: 135.4 g of light beige substance (89.5% of theoretical), melting point: from 169.5° C. (decomp.); purity:>98% HPLC peak area.
(1B)
25.02 g (0.46 mol) of sodium methoxide is added batchwise to a suspension of 60.5 g of (1A) (0.4 mol) in 400 mL of ethanol at 70° C.-75° C. and rinsed with 20 mL of ethanol. After 15 minutes stirring, 47.25 g (0.4 mol) of diethylcarbonate is added dropwise. After 3 hours reaction, the mixture is cooled to 40° C. and the ethanol is distilled off at 120 mbar and 40° C. A dark residue is obtained. This is dissolved in 350 mL of water at 40° C.-45° C. and, after heating to 70° C., first adjusted to pH 11 by the slow addition of semiconcentrated sodium hydroxide solution, then adjusted to pH 5.5 by acidification with concentrated hydrochloric acid and slowly cooled. The solution changes into a suspension which is filtered and washed several times with a total of 150 mL of cold water and 50 mL of ethanol. 88.7 g of damp substance is obtained, which is dried at 35° C. in vacuo. Yield: 62 g of dark substance (87.5% of theory); melting point: from 178° C. (decomp.); purity:>98% HPLC peak area.

Variant 2:

(1A)

In the reaction vessel, 41.3 g (0.35 mol) of 4-aminobenzonitrile and 36.5 g (0.53 mol) of hydroxylamine hydrochloride are placed in 175 mL of ethanol and heated to 60° C. 170.1 g (0.53 mol) of sodium ethoxide solution (~21% in ethanol) is slowly added dropwise to this suspension. The mixture is then stirred overnight at 60° C. On cooling to 0° C.-5° C., the substance is precipitated out, filtered off, and washed several times with a total of 70 mL of cold ethanol. Approximately 86 g of damp product is obtained. This is further processed directly.

(1B)

32 g (0.35 mol) of dimethylcarbonate is added to a suspension of 86 g of (1A) in 270 mL of ethanol. At 65° C.-75° C., 125 g (0.38 mol) of sodium ethoxide solution (~21% in ethanol) is added and the mixture is rinsed with 20 mL of ethanol. After 3 hours reaction, the mixture is cooled to 40° C. and the ethanol is distilled off at 120 mbar and 40° C. A dark residue is obtained. This is dissolved at 40° C.-45° C. in 280 mL of water and, after heating to 70° C., adjusted first to pH 11 by the slow addition of semiconcentrated sodium hydroxide solution, then adjusted to pH 3-4, or even more preferably to pH 2-3, by acidification with concentrated hydrochloric acid and slowly cooled. The solution changes into a suspension which is filtered and washed several times with a total of 50 mL of cold water and 20 mL of ethanol. Approximately 88 g of damp substance is obtained which is dried in vacuo at max. 50° C. Yield: 48 g of beige substance (77.5% of theory); melting point: from 178° C. (decomp.); purity:>98% HPLC peak area.

Example 2

Preparation of 2-[4-(1,2,4-oxadiazol-5-one-3-yl) phenylamino]acetic Acid (2)

Variant 1:

(2A)

At ambient temperature, 83.5 g (0.5 mol) of ethyl bromoacetate is metered into a suspension of 70.86 g (0.4 mol) of (1B) and 26.5 g (0.25 mol) of sodium carbonate in 600 mL of water/isopropanol and stirred overnight. The reaction mixture is reddish-brown to orange. The suspension cooled to 0° C. is suction filtered, washed in several batches with 300 mL of water and 150 mL of ethanol (106 g of damp light brown substance), and dried in vacuo at 35° C. Yield: 92.44 g of brownish substance (87.7% of theory); melting point: from 186.1° C. (decomp.) purity:>98% HPLC peak area.

(2B)

The ester (2A) thus obtained (86.9 g, 0.33 mol) is suspended in 400 mL of water and at RT 120 g of 45% NaOH is slowly added dropwise. The suspension goes into solution and is reddish (pH 12.5). It is heated to ~60° C. and saponified for 1 hour. The solution obtained is combined batchwise with HCl (37%, or even more preferably concentrated HCl) until a pH of 5 is achieved. The mixture is cooled to 0° C. The solid suction filtered and washed in several batches with a total of 400 mL of cold water as well as 40 mL each of cold ethanol and MtBE. 81.4 g of damp dark substance is obtained. It is dried in vacuo at 35° C. Yield: 76.7 g substance (98% of theory); melting point: from 193° C. (decomp.); purity:>99% HPLC peak area.

Variant 2:

(2A)

At 45° C., 60.2 g (0.36 mol) of ethyl bromoacetate is metered into a suspension of 53.2 g (0.3 mol) of (1B) and 19.1 g (0.18 mol) of sodium carbonate in 500 mL of water/ethanol (90:10 to 95:5) and optionally stirred overnight. The reaction mixture is reddish-brown to orange. The suspension cooled to 0° C. is suction filtered, washed in several batches with 100 mL of ethanol, and dried in vacuo at max. 50° C. Yield: 69.5 g of brownish-beige substance (87.7% of theory); melting point: from 186.1° C. (decomp.) purity:>98% HPLC peak area.

(2B)

The ester (2A) thus obtained (86.9 g, 0.33 mol) is suspended in 400 mL of water or even more preferably ethanol/water (1:1) and at RT 120 g of 45% NaOH is slowly added dropwise. The suspension goes into solution and is reddish (pH 12.5). It is heated to ~60° C. and saponified for 1 hour. HCl (37%, or even more preferably concentrated HCl) is added batchwise to the solution obtained until a pH of 3 is achieved. The mixture is cooled to 0° C. The solid is suction filtered and washed in several batches with a total of 400 mL of cold water as well as 40 mL of cold ethanol. 81.4 g of damp substance is obtained. It is dried in vacuo at 35° C. Yield: 76.7 g substance (98% theory); melting point: from 193° C. (decomp.); purity:>99% HPLC peak area.

Example 3

Preparation of 1-methyl-2-[N-[4-(1,2,4-oxadiazol-5-one-3-yl)phenyl]aminomethyl]benzimidazol-5-ylcarboxylic acid-N-(2-pyridyl)-N-(2-ethoxycarbonylethyl)amide (3)

Variant A: CDI as coupling reagent 11.35 g (70 mmol) of 1,1'-carbonyldiimidazole is suspended in 100 mL of THF and heated to 50° C. 14.23 g (60.5 mmol) of (2B) is added batchwise. 17.1 g (50 mmol) of AMBPA is dissolved in 37 mL of THF with heating to 50° C. After approximately 90 minutes, the suspension is metered into the solution of AMBPA and rinsed with 20 mL of THF. The reaction mixture is stirred for approximately 18 hours and then refluxed after the addition of 100 mL of acetic acid, so that the THF is distilled off. After approximately 1 hour, 400 mL of water is added and the mixture is stirred. The solution is cooled, the pink solid substance precipitated is filtered off and washed in 2 batches with 20 mL of water and dried in vacuo at max 50° C. The isolated substance is the diacetate of (3). Yield: 24.8 g of substance (75% theory); melting point: from 167° C. with decomp. (DSC); purity: >95% HPLC peak area.

Varient B: PPA as coupling reagent 34.2 g (0.1 mol) of AMBPA, 27.5 g (0.12 mol) of (2B), and 30.3 g (0.23 mol) of DIPEA are placed in 170 mL of THF and cooled to somewhat below ambient temperature. Then 85 g (0.13 mol) of PPA (as a ~50% solution in ethyl acetate) are metered in. The mixture is stirred for another 90 minutes and then the solvent is distilled off. Towards the end, 73.5 g of acetic acid is added and the mixture is heated to an internal temperature of 90° C. Then 400 mL of ethanol or preferably 400 mL of ethanol/water (ca. 85:15) is added and the mixture is filtered hot. The solution is cooled, and the precipitated solid substance is filtered off and washed with 50 mL of ethanol in 2 batches and dried in vacuo at max 50° C. The isolated substance is the diacetate of (3). Yield: 56 g of substance (85% of theory); melting point: from 167° C. with decomp. (TLC); purity:>95% HPLC peak area.

Variant C: Pivaloyl chloride as coupling reagent 96 g (0.41 mol) of (2B) is suspended at 0° C. in 250 mL of NMP and 550 mL of THF. The thin suspension is combined successively with 48 g (0.4 mol) of pivaloyl chloride and 52 g (0.4 mol) of DIPEA and stirred for 30 minutes. Then 125 g (0.36 mol) of AMBPA dissolved in 800 mL of acetic acid are added and the reaction mixture is refluxed for 3 hours. THF is distilled off under a slight vacuum and 1600 mL of water are metered in while it is warm. The solid is isolated at 5° C., washed with 550 mL of water and dried overnight in the circulating air dryer at max. 50° C. Yield: 183 g (76%); purity:>95% HPLC peak area.

Example 4

Preparation of 1-methyl-2-[N-[4-amidinophenyl] aminomethyl]benzimidazol-5-ylcarboxylic acid-N-(2-pyridyl)-N-(2-ethoxycarbonylethyl)amide (4)

Variant A: Hydrogenation of (3) in ethanol 37.3 g (56.4 mmol) of (3) is dissolved in 900 mL of ethanol and, after the addition of 10 mL of acetic acid, hydrogenated with 4 g of water-dampened 10% Pd/C at RT and at 2 bar hydrogen. The catalyst is filtered off and 17 g (89.4 mmol) of PTSA dissolved in 180 mL of ethanol is added to the filtrate. The tosylate of (4) is precipitated out, filtered off, and washed again with 150 mL of ethanol in several batches. Damp substance is obtained which is dried in vacuo at 35° C. Yield: 34.5 g of light beige substance (91.3% of theory); melting point: 187° C. (TLC); purity:>98% HPLC peak area.

Variant B: Hydrogenation of (3) in ethanol/water 37.3 g (56.4 mmol) of (3) is dissolved in 400 mL of ethanol/ water (90:10) and hydrogenated with 4 g of water-dampened 10% Pd/C at RT and at 2 bar hydrogen. The catalyst is filtered off and 11.5 g (60.6 mmol) of PTSA is added to the filtrate. On evaporation, the tosylate of (4) is precipitated out. The suspension is cooled and then substance is filtered off and washed in several batches with 150 mL of ethanol/water. Damp substance is obtained which is dried in vacuo at 35° C. Yield: 33.7 g of light beige substance (89% theory); melting point: 187° C. (TLC); priority:>98% HPLC peak area.

Variant C: Hydrogenation of (3) in THF/water 30.0 g (45.3 mmol) of (3) is dissolved at ambient temperature in 90 mL of THF/water (1:1), combined with 4 g of water-dampened 10% Pd/C and hydrogenated at 4 bar and 60° C. The catalyst is filtered off, washed again approximately 40 mL of THF/water (1:1) and the filtrate is used in the next step without working up or is isolated as described above by addition of 13.6 g (72 mmol) of PTSA dissolved in 100 mL of water and cooling.

Example 5

Preparation of 1-methyl-2-[N-[4-(N-(n-hexyloxycarbonylamidino)phenyl]aminomethyl]benzimidazol-5-yl-carboxylic acid-N-(2-pyridyl)-N-(2-ethoxycarbonylethyl)amide (5)

The compound obtained according to Example 4 is reacted in known manner with hexyl chloroformate in the presence of a base.

Variant A: Acylation of (4) in acetone/water 55 g (81.9 mmol) of (4) dissolved in 437 mL of acetone and 273 mL of water is combined with 16.4 g (99.6 mmol) of hexyl chloroformate in the presence of 34 g (246 mmol) of potassium carbonate at a temperature of about 15° C. After the end of the reaction, the precipitated product is filtered off and washed with acetone/water. If necessary it may be dissolved once more in approximately 270 mL of acetone with heating and then filtered. After filtration, the substance is crystallized again by the addition of 220 mL of water. The isolated substance is dried in vacuo at 45° C. Yield: 42 g-48 g (82-94%)

Variant B: Acylation of (4) in acetone/water with phase separation 55 g (81.9 mmol) of (4) dissolved in 437 mL of acetone and 273 mL of water is combined with 16.4 g (99.6 mmol) of hexyl chloroformate in the presence of 67 g (486 mmol) of potassium carbonate at a temperature of about 15° C. After the end of the reaction, the suspension is heated to approximately 50° C. After phase separation, the aqueous phase is discarded and acetone is replaced by 440 mL of ethyl acetate. The then separated aqueous phase is discarded and the organic phase is washed in several batches with diluted potassium carbonate solution and finally water. The product is crystallized upon cooling, isolated and washed with ethyl acetate. The isolated substance is dried in vacuo at 45° C. Yield: 42 g-48 g (82%-94%)

Example 6

Preparation of 1-methyl-2-[N-[4-(N-n-hexyloxycarbonylamidino)phenyl]aminomethyl]benzimidazol-5-ylcarboxylic acid-N-(2-pyridyl)-N-(2-ethoxycarbonylethyl)amide (5) mesylate 100 g (0.16 mmol) of compound (5) is dissolved in 890 mL of acetone with heating and combined with a solution of 15 g (0.16 mol) of methanesulfonic acid in 200 mL of acetone. The solution is filtered and after the addition of 77 mL of acetone cooled to approximately 20° C. The precipitated product is isolated and washed against with acetone. Then it is dried at max. 50° C. in the vacuum drying cupboard. Yield: 103 g-113 g (90%-98%).

We claim:

1. A compound of formula (III)

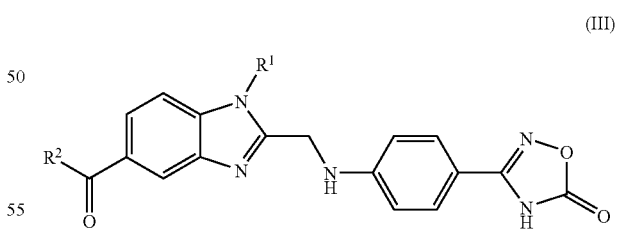

(III)

wherein:
R$^1$ is a C$_{1-6}$-alkyl or C$_{3-7}$-cycloalkyl group; and
R$^2$ is
(i) a C$_{1-6}$-alkyl group or a C$_{3-7}$-cycloalkyl group optionally substituted by a C$_{1-3}$-alkyl group, wherein the C$_{1-3}$-alkyl group is optionally substituted by a carboxyl group or
(ii) an R$^{21}$NR$^{22}$ group, wherein:
R$^{21}$ is a C$_{1-6}$ alkyl group optionally substituted by a carboxy, C$_{1-6}$ alkoxycarbonyl, benzyloxycarbonyl, C$_{1-3}$-alkylsulfonylaminocarbonyl, phenylsulfonylaminocarbonyl, trifluorosulfonylamino, trifluorosulfonylaminocarbonyl, or 1H-tetrazolyl group, a $C_{2-4}$-alkyl group substituted by a hydroxy, phenyl-$C_{1-3}$-alkoxy, carboxy-$C_{1-3}$-alkylamino, $C_{1-3}$-alkoxycarbonyl-$C_{1-3}$-alkylamino, N-($C_{1-3}$-alkyl)-carboxy-$C_{1-3}$-alkylamino, or N-($C_{1-3}$-alkyl)-$C_{1-3}$-alkoxycarbonyl-$C_{1-3}$-alkylamino group, wherein the α-carbon atom to the adjacent nitrogen atom thereof is not substituted, or a piperidinyl group optionally substituted by a $C_{1-3}$-alkyl group, and $R^{22}$ is a hydrogen atom,

- a $C_{1-6}$-alkyl group,
- a $C_{3-7}$-cycloalkyl group optionally substituted by a $C_{1-3}$-alkyl group,
- a $C_{3-6}$-alkenyl, or $C_{3-6}$-alkynyl group, wherein an unsaturated moiety of the $C_{3-6}$-alkenyl or $C_{3-6}$-alkynyl group is not linked directly to the nitrogen atom of the $R^{21}NR^{22}$ group,
- a phenyl group optionally substituted by a fluorine, chlorine, or bromine atom or by a $C_{1-3}$-alkyl or $C_{1-3}$-alkoxy group, or
- a benzyl, oxazolyl, isoxazolyl, thiazolyl, isothiazolyl, pyrazolyl, pyridinyl, pyrimidinyl, pyrazinyl, pyridazinyl, pyrrolyl, thienyl, or imidazolyl group optionally substituted by a $C_{1-3}$-alkyl group; or $R^{21}$ and $R^{22}$ together with the nitrogen atom between them are a 5- to 7-membered cycloalkyleneimino group optionally substituted by a carboxy or $C_{1-4}$-alkoxycarbonyl group, to which a phenyl ring is optionally additionally fused.

2. The compound of formula (III) according to claim 1, wherein:

$R^1$ is a $C_{1-3}$-alkyl group; and
$R^2$ is an $R^{21}NR^{22}$ group, wherein:
$R^{21}$ is a $C_{1-3}$ alkyl group optionally substituted by a carboxy or $C_{1-3}$ alkoxycarbonyl, and
$R^{22}$ is a hydrogen atom, a $C_{1-3}$-alkyl group, or a pyridyl group optionally substituted by a $C_{1-3}$-alkyl group.

3. The compound of formula (III) according to claim 2, wherein:

$R^1$ is a methyl group;
$R^2$ is an $R^{21}NR^{22}$ group, wherein:
$R^{21}$ is an ethyl group substituted by an ethoxycarbonyl group, and
$R^{22}$ is a pyridin-2-yl group.

4. 2-[4-(1,2,4-Oxadiazol-5-one-3-yl)phenylamino]acetic acid.

* * * * *